US009802725B2

(12) United States Patent
Poppi et al.

(10) Patent No.: US 9,802,725 B2
(45) Date of Patent: Oct. 31, 2017

(54) ELECTRON BEAM STERILIZATION UNIT FOR PROCESSING FOOD PACKAGING MATERIAL

(71) Applicant: TETRA LAVAL HOLDINGS & FINANCE S.A., Pully (CH)

(72) Inventors: Luca Poppi, Formigine (IT); Roberto Fontanesi, Traversetolo (IT); Marco Lavalle, Formigine (IT); Eros Ferrari, Modena (IT)

(73) Assignee: TETRA LAVAL HOLDINGS & FINANCE S.A., Pully (CH)

( * ) Notice: Subject to any disclaimer, the term of this patent is extended or adjusted under 35 U.S.C. 154(b) by 0 days.

(21) Appl. No.: 15/032,922

(22) PCT Filed: Dec. 16, 2014

(86) PCT No.: PCT/EP2014/078021
§ 371 (c)(1),
(2) Date: Apr. 28, 2016

(87) PCT Pub. No.: WO2015/101483
PCT Pub. Date: Jul. 9, 2015

(65) Prior Publication Data
US 2016/0251099 A1   Sep. 1, 2016

(30) Foreign Application Priority Data

Dec. 30, 2013  (EP) .................................... 13199860

(51) Int. Cl.
*G01N 23/00* (2006.01)
*B65B 55/08* (2006.01)
(Continued)

(52) U.S. Cl.
CPC .............. *B65B 55/08* (2013.01); *A61L 2/087* (2013.01); *A61L 2202/23* (2013.01); *G21K 5/02* (2013.01)

(58) Field of Classification Search
CPC ......... B65B 55/00; B65B 55/02; B65B 55/08; B65B 55/12; B65B 55/16; A61L 2/00;
(Continued)

(56) References Cited

U.S. PATENT DOCUMENTS

2006/0147258 A1*  7/2006  Naslund ................... G21K 1/06
                                                              403/321
2008/0273919 A1    11/2008  Naslund et al.
(Continued)

FOREIGN PATENT DOCUMENTS

EP      2 462 953 A1   6/2012
WO   WO 2004/111469 A1  12/2004

OTHER PUBLICATIONS

International Search Report (PCT/ISA/210) dated Feb. 5, 2015, by the European Patent Office as the International Searching Authority for International Application No. PCT/EP2014/078021.
(Continued)

*Primary Examiner* — Jason McCormack
(74) *Attorney, Agent, or Firm* — Young & Thompson

(57) ABSTRACT

An electron beam sterilization unit for processing food packaging material, the unit having a frame; at least one electron beam emitter fitted to the frame, along the path of the material for processing, and having a flange for connection to the frame; and a locking device, which is fitted to the frame, and has thrust devices for exerting a lock force on the flange in a given first direction, and for locking the emitter, with respect to the frame, in a given work position, and actuating devices for activating the thrust devices and which are defined by toggle devices.

18 Claims, 6 Drawing Sheets

(51) Int. Cl.
*A61L 2/08* (2006.01)
*G21K 5/02* (2006.01)

(58) Field of Classification Search
CPC .......... A61L 2/0029; A61L 2/007; A61L 2/08; A61L 2/087
USPC ..................... 250/455.11, 453.11, 454.11
See application file for complete search history.

(56) References Cited

U.S. PATENT DOCUMENTS

2011/0198513 A1* 8/2011 Holm ................ A61L 2/087
250/492.3
2012/0145929 A1 6/2012 Nishino et al.

OTHER PUBLICATIONS

Written Opinion (PCT/ISA/237) dated Feb. 5, 2015, by the European Patent Office as the International Searching Authority for International Application No. PCT/EP2014/078021.

* cited by examiner

ELECTRON BEAM STERILIZATION UNIT FOR PROCESSING FOOD PACKAGING MATERIAL

BACKGROUND OF THE INVENTION

Field of the Invention

The present invention relates to an electron beam sterilization unit for processing food packaging material.

Description of the Related Art

In the food industry, and particularly in the packaging of numerous pourable food products, such as fruit juice, milk, wine, etc., automatic packaging machines are used to produce aseptic packages from sheet packaging material, which is normally in the form of pre-cut blanks or a continuous strip and is subjected to a series of longitudinal folding and sealing operations to form a continuous tube of packaging material which, once filled, is sealed and cut transversely into individual packages.

Before it reaches the packaging machine, the sheet material is fed through a sterilization unit, on which it is processed to destroy microorganisms, to ensure the packaged products are microbiologically safe, and to effectively preserve their organoleptic and nutritional properties.

For this purpose, various types of sterilization units have been devised, the most advantageous of which are those employing electron beams to irradiate the two opposite faces of a moving web of packaging material.

Known electron beam sterilization units normally comprise a frame; a channel formed through the frame to guide the web of packaging material in a given direction; and two electron beam emitters fitted to the frame, on opposite sides of the web guide channel. Each emitter comprises, in known manner, a vacuum tube in which the electrons, emitted by a cathode, are accelerated by an electrostatic field and are shot out of the tube, in the form of electron beams, through an irradiation window, closed by a thin plate normally made of a foil of titanium, aluminium, silicon, etc., to strike a respective face of the packaging material as this moves along the guide channel.

An important and highly delicate aspect of known sterilization units of the type described above is the way in which the emitters are locked to the frame. In fact, it is essential that the system for assembling and locking the emitters to the frame should allow for installing and removing them easily and safely whenever they need changing or servicing, and for also locking the emitters in the work position quickly and easily, but at the same time in controlled manner, to avoid endangering the integrity of the emitter and in particular the delicate foil closing the electron beam irradiation window.

A sterilization unit of the type described above is known, for example, from the Applicant's International Patent Application No. WO2004/111469, in which the locking system comprises, for each emitter, a cam device, which, by moving an operating member, moves a pusher crosswise to the travelling plane of the material. The pusher in turn acts on a flange on the emitter, facing the channel, to push and seal the flange onto a portion of the frame and so lock the emitter in the work position.

Though effective, the locking system described above has several drawbacks, due to the cam device failing to ensure safe, irreversible grip in any stress condition, and due to the design of the locking system whereby, once the flange is fastened onto the frame, the rigid connection formed between the flange and the frame allows no compensation of any 'static' deformation of the flange caused, for example, by unevenness of the gripping surfaces, or of any 'dynamic' deformation of the flange caused by in-service thermal expansion. This may result in stress within the body of the emitter, which in turn may result in bending of the foil closing the irradiation window, and therefore in malfunctioning of or damage to the emitter.

BRIEF SUMMARY OF THE INVENTION

It is an object of the present invention to provide an electron beam sterilization unit, for processing food packaging material, designed to eliminate the above drawbacks.

According to the present invention, there is provided an electron beam sterilization unit, for processing food packaging material.

BRIEF DESCRIPTION OF THE DRAWINGS

A non-limiting embodiment of the present invention will be described by way of example with reference to the attached drawings, in which.

DETAILED DESCRIPTION OF THE PREFERRED EMBODIMENTS

Figure 1:
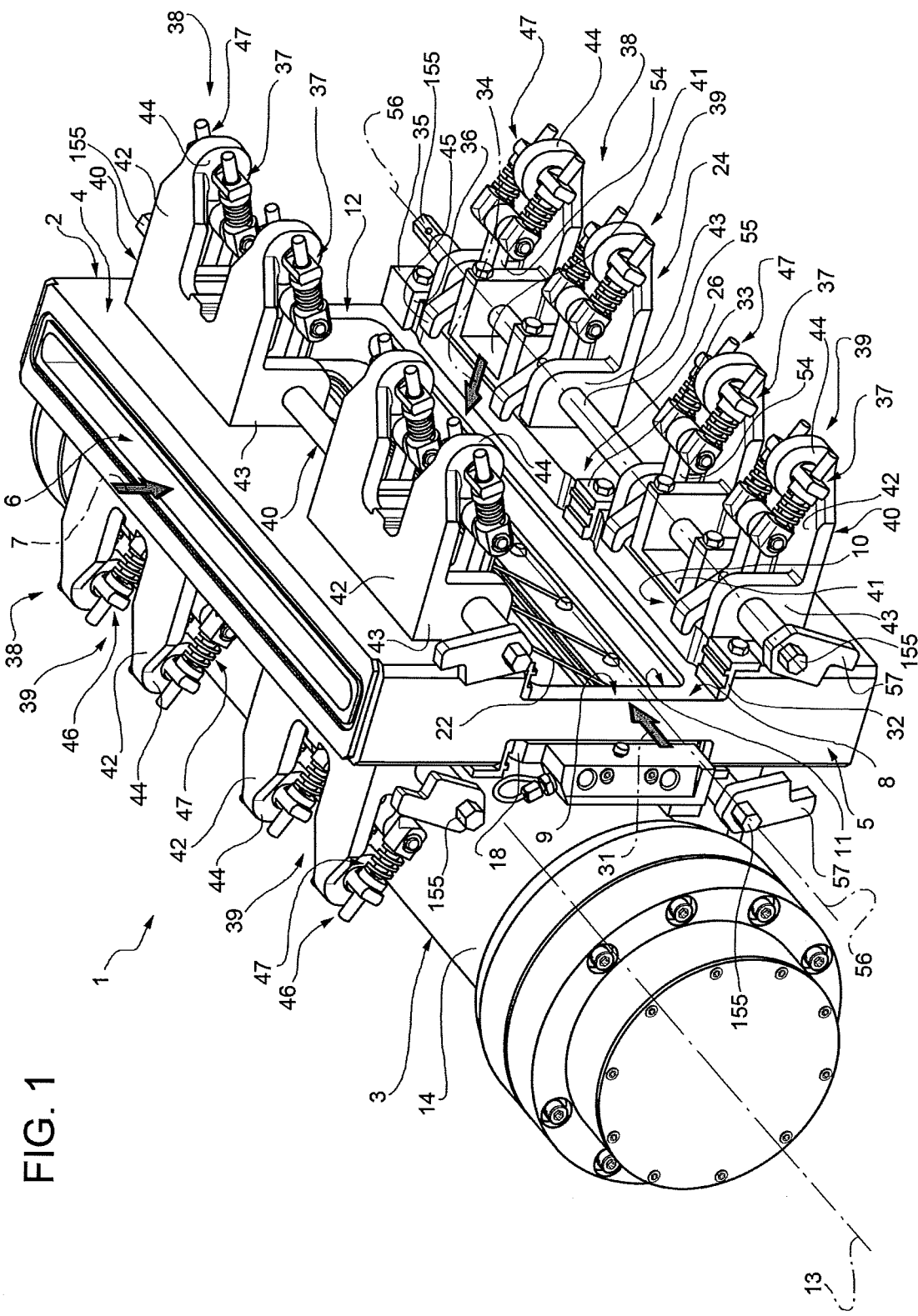
FIG. 1 shows a view in perspective, with parts removed for clarity, of a preferred embodiment of the sterilization unit according to the present invention.

Number 1 in FIG. 1 indicates as a whole an electron beam sterilization unit for processing sheet packaging material from which to produce sealed aseptic packages of food products, in particular pourable products, such as milk, fruit juice, wine, etc.

In an industrial plant, the sterilization unit normally forms part of an automatic packaging machine, and is fed with a web of packaging material, which is normally unwound off a reel and, downstream from the sterilization unit, is fed to a forming unit where it is folded and sealed longitudinally to form a continuous tube, which is then filled with the food product for packaging, and is sealed and cut transversely into individual packs, which are then folded to form individual finished packages.

Figure 2:
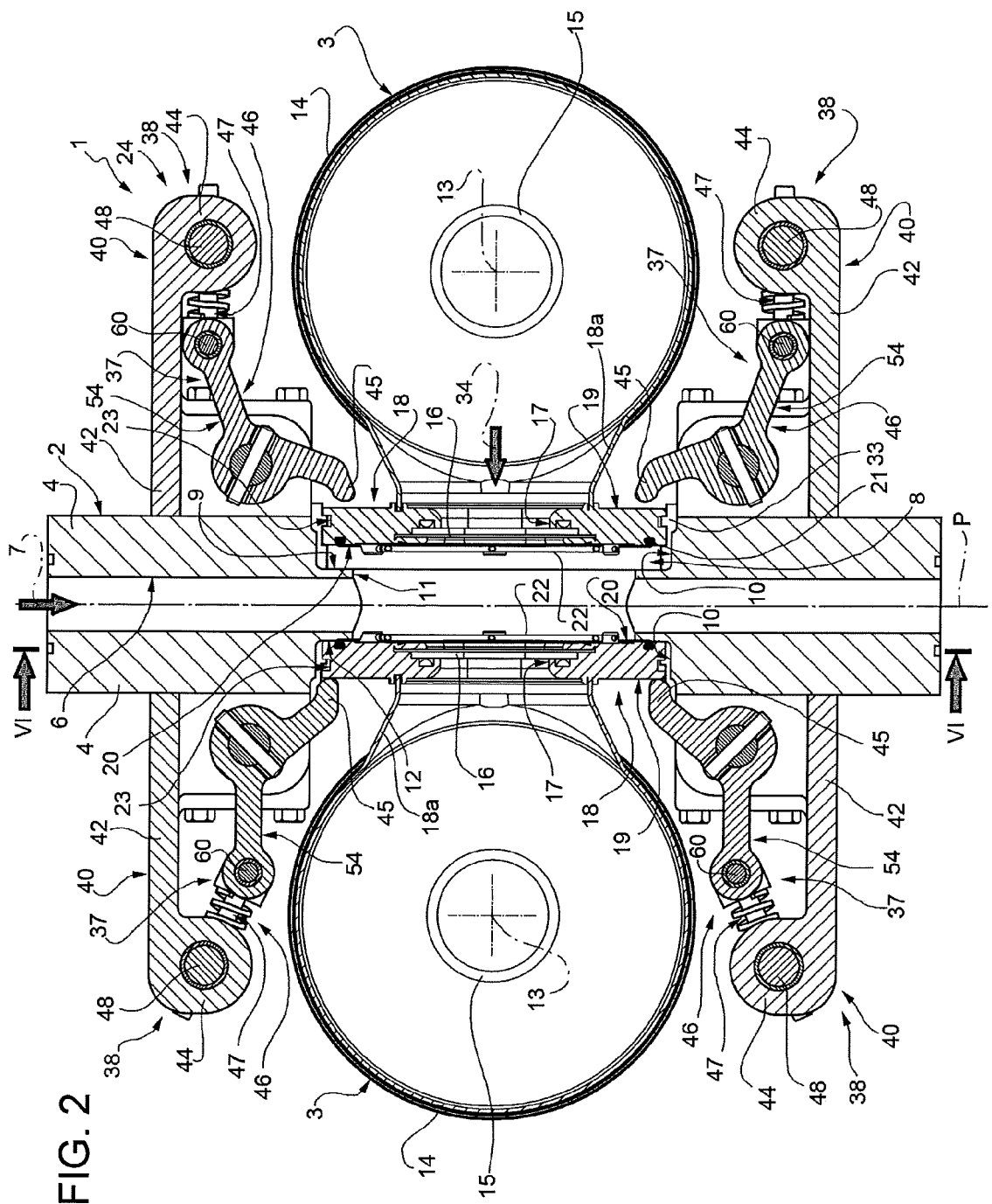
FIG. 2 shows a cross section of the FIG. 1 unit.

As shown in FIGS. 1 and 2, sterilization unit 1 comprises a frame 2 supporting two electron beam emitters 3 on opposite sides of the path travelled by a web of packaging material (not shown). Frame 2 is defined by a generically parallelepiped-shaped box body bounded laterally by two flat, opposite, substantially vertical first lateral walls 4, and by two opposite second lateral walls 5 crosswise to lateral walls 4 and defining within them a channel 6, which has a roughly rectangular cross section and a substantially vertical longitudinal plane of symmetry P, and in use is traversed by the web of packaging material (not shown) in a substantially vertical travelling direction 7.

A centre portion of each lateral wall 4 has a rectangular recess 8, which is specular to the recess of the other lateral wall 4 with respect to the plane of symmetry P of channel 6. The rectangular recess 8 extends crosswise to direction 7 over the entire width of lateral wall 4, is open at its longitudinal ends through lateral walls 5, and is bounded internally by a flat rear surface 9 parallel to plane P, and by two opposite lateral surfaces 10 perpendicular to rear surface 9 and crosswise to travelling direction 7. A through opening 11 is formed in each rear surface 9 to connect respective recess 8 to channel 6, and defines, on respective rear surface 9, an annular portion extending about opening 11 and defining, as explained below, a locating rim 12 by which to position a respective emitter 3.

Figure 6:
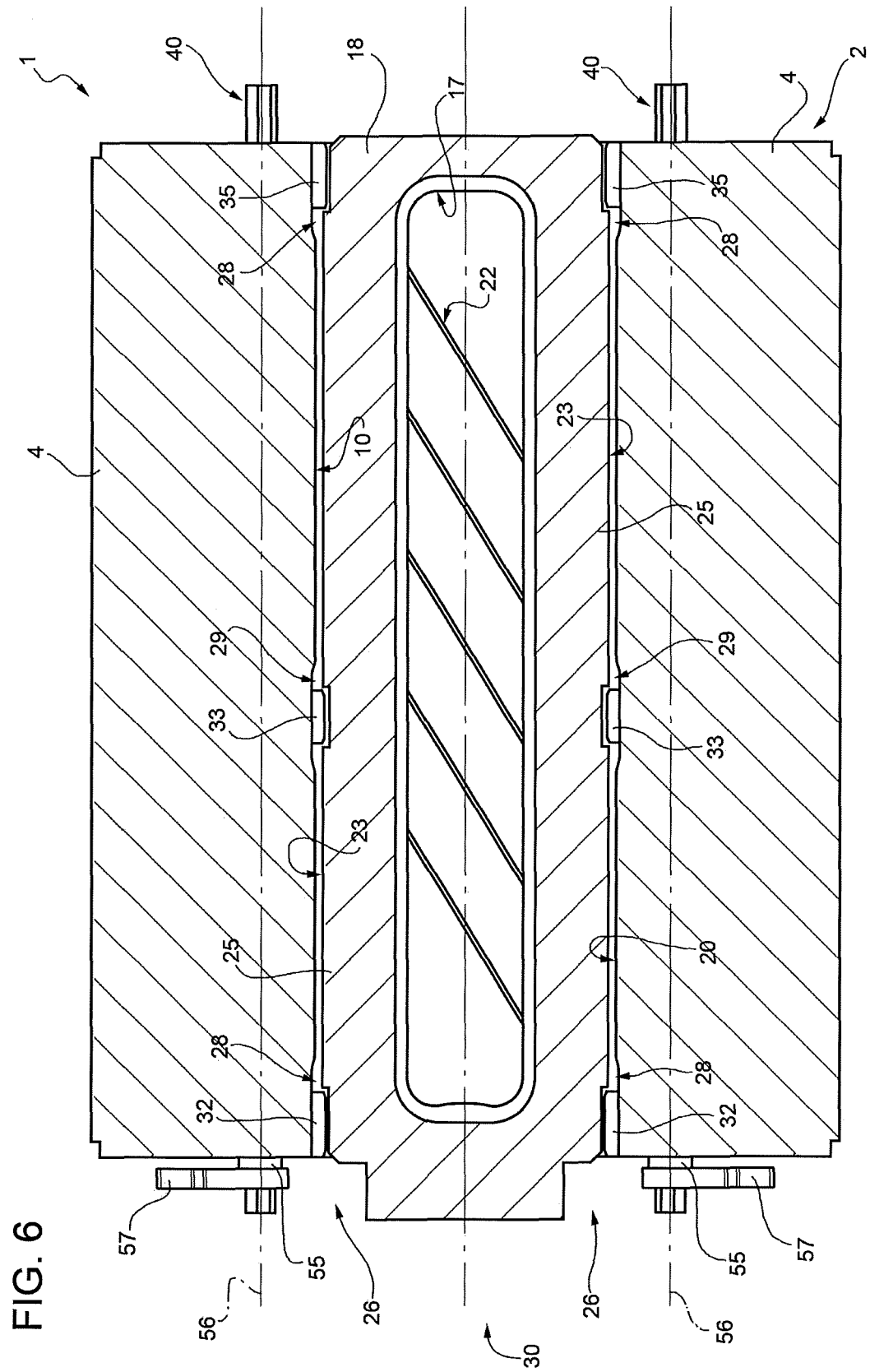
FIG. 6 shows a section along line VI-VI in FIG. 2.

As shown in FIGS. 1, 2 and 6, each emitter 3 is defined by a known linear electron accelerator, and is in the form of a generically cylindrical body. The body has a longitudinal axis 13 and comprises an outer casing 14 housing a gun 15, where the electrons, emitted by a radiation source, are accelerated in a vacuum into beams by the application of an electric field generated by a voltage between the radiation source and a foil 16.

Foil 16 is grounded electrically, is located outside gun 15, and is normally defined by a sheet of titanium, aluminium, silicon, etc., of a few μm in thickness.

Figure 5:
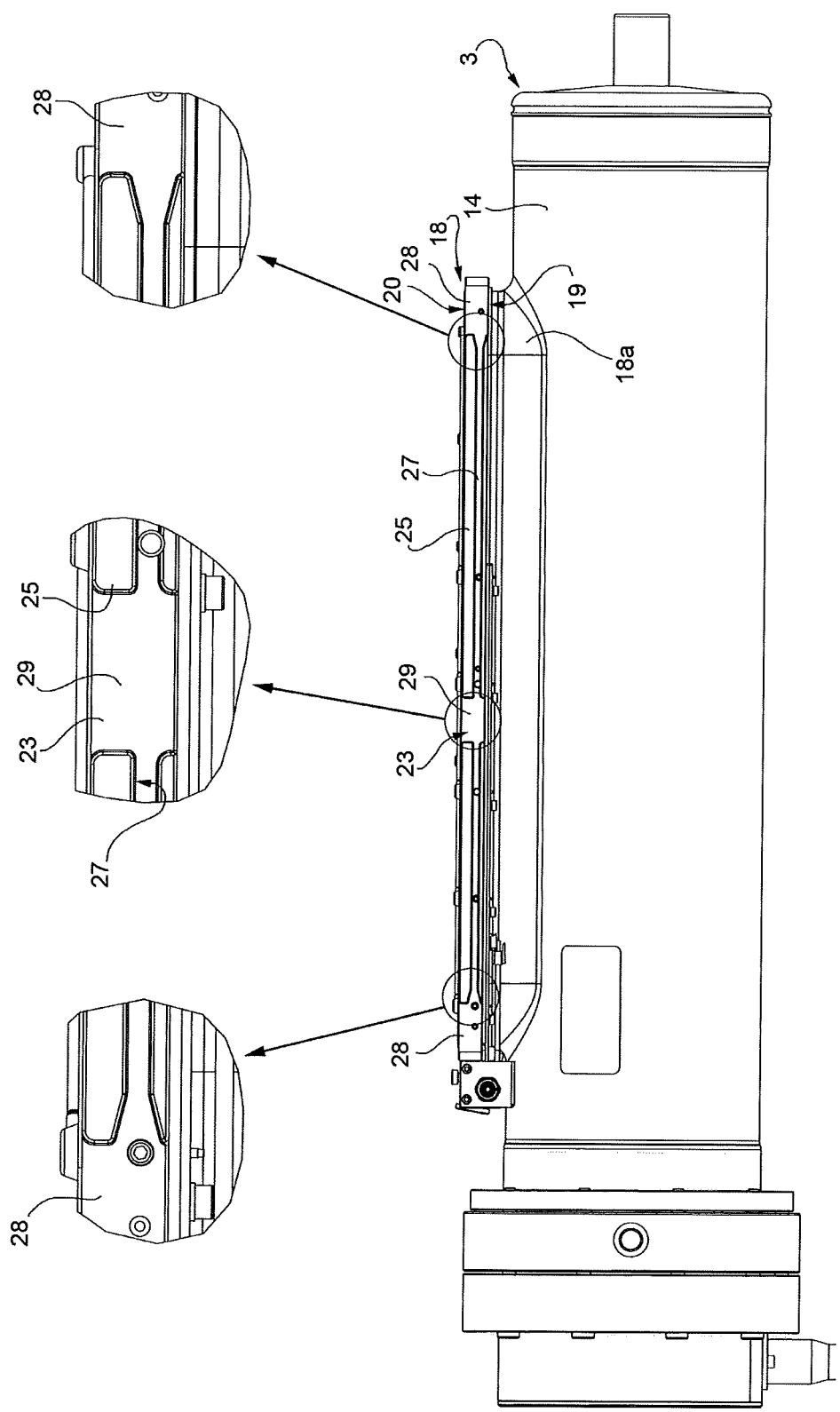
FIG. 5 shows a side view of a detail in FIG. 2.

More specifically, and with reference to FIGS. 2, 5 and 6, foil 16 of each emitter 3 closes a respective window 17 formed through a rectangular annular flange 18. Flange 18 extends alongside gun 15, lies in a plane parallel to longitudinal axis 13 and to the plane on which locating rim 12 lies, and is supported rigidly by a contoured portion 18a of casing projecting transversely outwards from casing 14. Window 17 of each flange 18 is roughly the same shape and size as opening 11, and is bounded laterally by two opposite, flat, parallel annular surfaces, of which a first annular surface 19 faces emitter 3, and a second annular surface 20 faces away from emitter 3. When emitter 3 is positioned on frame 2 in the work position (shown on the left in FIG. 2), annular surface 20 is pushed onto rim 12 surrounding opening 11. Surface 20 has an annular groove surrounding window 17 and engaged by an annular seal 21. And, on the annular surface 20 side, window 17 of each flange 18 is closed by a grille 22 to protect respective foil 16 from damage by external objects.

Along its free longitudinal edges, each flange 18 is bounded by two sides 23, which lie in respective planes parallel to longitudinal axis 13 and perpendicular to annular surfaces 19 and 20, and, as explained below, are designed to engage lateral surfaces 10 of a respective recess 8 to connect respective emitter 3 to frame 2.

In addition to supporting a respective foil 16, each flange 18 therefore also defines an interface by which to fit respective emitter 3 to frame 2. Each emitter 3 is fitted removably to frame 2 and, once installed on frame 2, is movable between an idle position (shown on the right in FIG. 2) and the aforementioned work position. In the idle position, longitudinal axis 13 is parallel to plane P and crosswise to travelling direction 7, and flange 18 is inserted inside a respective recess 8 and at a given distance from rim 12; in the work position, in which longitudinal axis 13 is still parallel to plane P and crosswise to travelling direction 7, flange 18 is sealed to rim 12, and emitter 3 is locked firmly in position by a locking device 24 as described below.

As shown in FIGS. 1, 5 and 6, to insert and fit respective emitter 3 to frame 2, each flange 18 has two runners 25, each of which is located on a respective side 23 of flange 18 and slides axially along a respective straight guide 26 on frame 2.

More specifically, each runner 25 (FIGS. 3 and 5) is defined by a raised longitudinal member, which projects from a respective side 23, is parallel to longitudinal axis 13 of respective emitter 3, and has a straight longitudinal groove 27, which is parallel to longitudinal axis 13, has two flared end portions to simplify insertion of runner 25 inside respective guide 26, and is bounded at the bottom by respective side 23.

Each runner 25 extends along the whole length of respective side 23, except for two end portions 28 of side 23 of roughly the same length. Each runner 25 is also divided into two portions separated by a gap 29 of roughly the same length as each end portion 28.

As shown in FIGS. 1, 2 and 6, each guide 26 cooperating with a respective runner 25 is mounted on a lateral surface 10 of a respective recess 8, is identical to the guide 26 mounted on the other lateral surface 10 and cooperating with the other runner 25, and defines with the other guide 26 a guide device 30 for guiding flange 18 along recess 8 in an insertion direction 31 perpendicular to travelling direction 7, and for supporting emitter 3 on frame 2.

Each guide 26 comprises two blocks 32 and 33 fitted rigidly to one end and to an intermediate portion of lateral surface 10 respectively. On the side facing inwards of recess 8, each block 32, 33 has two ribs, which extend parallel to insertion direction and form on respective block 32, 33 a grooved profile along which respective runner 25 slides, and which, as flange 18 moves in insertion direction 31, defines a positive connection in a direction 34 perpendicular to insertion direction 31 and travelling direction 7, i.e. a connection that fixes flange 18 to frame 2 in direction 34.

For each guide 26, guide device 30 also comprises a stop 35, which is defined by a block fixed to the opposite end of lateral surface 10 to that supporting block 32, and which, on the side facing blocks 32 and 33, has a shoulder 36 perpendicular to lateral surface and which rests against an axial end portion of runner 25.

As shown in FIG. 6, blocks 32, 33 and stop 35 are spaced along lateral surface 10 like portions 28 and gap 29, so that, when emitter 3 is moved into the idle position, block 32 and stop 35 loosely engage respective portions 28, and block 33 loosely engages gap 29. So, in the idle position, block 32 and stop 35 engaging respective portions 28, and block 33 engaging gap 29 define a transverse guide allowing flange 18 to be moved freely, by an external force produced by locking device 24 in direction 34 (shown in FIG. 1), towards rear surface 9 of recess 8 and so move emitter 3 into the work position.

In connection with the above, and with particular reference to FIG. 6, it should be pointed out that block 32 and stop 35 of each guide 26 are of the same thickness, project from respective lateral surfaces 10, and have respective coplanar end surfaces which, when emitter 3 is in the idle and work positions, rest at the front against respective sides 23 to define respective support and slide surfaces for flange 18. Each block 33, on the other hand, is thinner than blocks 32 and stops 35, so that, when emitter 3 is in the work position, block 33, as opposed to contacting side 23, is separated from it by a gap of given size. In the work position, flange 18 of each emitter 3 is therefore only supported at its longitudinal ends, while the whole of its centre portion is detached from lateral surfaces 10 of respective recess 8. This prevents or at least reduces the likelihood of deformation of flange 18, caused by in-service thermal expansion of flange 18, being transmitted to, and producing serious overstress in, frame 2.

As stated, each emitter 3 is locked in the work position by locking device 24 (FIG. 1) exerting pressure on flange 18 in direction 34. In addition to locking emitter 3 in the work position, locking device 24 also provides for moving emitter 3 in direction 34 from the idle position to the work position.

As shown in FIGS. 1 and 2, for each emitter 3, locking device 24 comprises a number of thrust mechanisms 37 mounted on frame 2 and divided into two groups 38, which are located on opposite sides of recess 8 and each comprise four thrust mechanisms 37 grouped into two identical pairs 39 operated by a common control member.

Each pair 39 of thrust mechanisms 37 is mounted on lateral wall 4 of frame 2, close to a respective outer longitudinal edge of recess 8, by a respective L-shaped bracket 40, which comprises a connecting portion 41 fixed rigidly to lateral wall 4, and a plate 42 projecting outwards of frame 2 from lateral wall 4 and having, close to lateral wall 4, two lateral portions 43 bent squarely with respect to plate 42 and extending towards recess 8 from plate 42.

Close to its free end, each plate 42 has two appendages 44 defined by two flat plates projecting transversely from plate 42 towards recess 8 and lying in respective parallel planes perpendicular to plane P.

The two brackets 40 of each group 38 are spaced apart along the outer longitudinal edge of recess 8, so that one is located at the portion of lateral surface 10 between blocks 32 and 33, and the other is located at the portion of lateral surface 10 between block 33 and stop 35.

Figure 3:
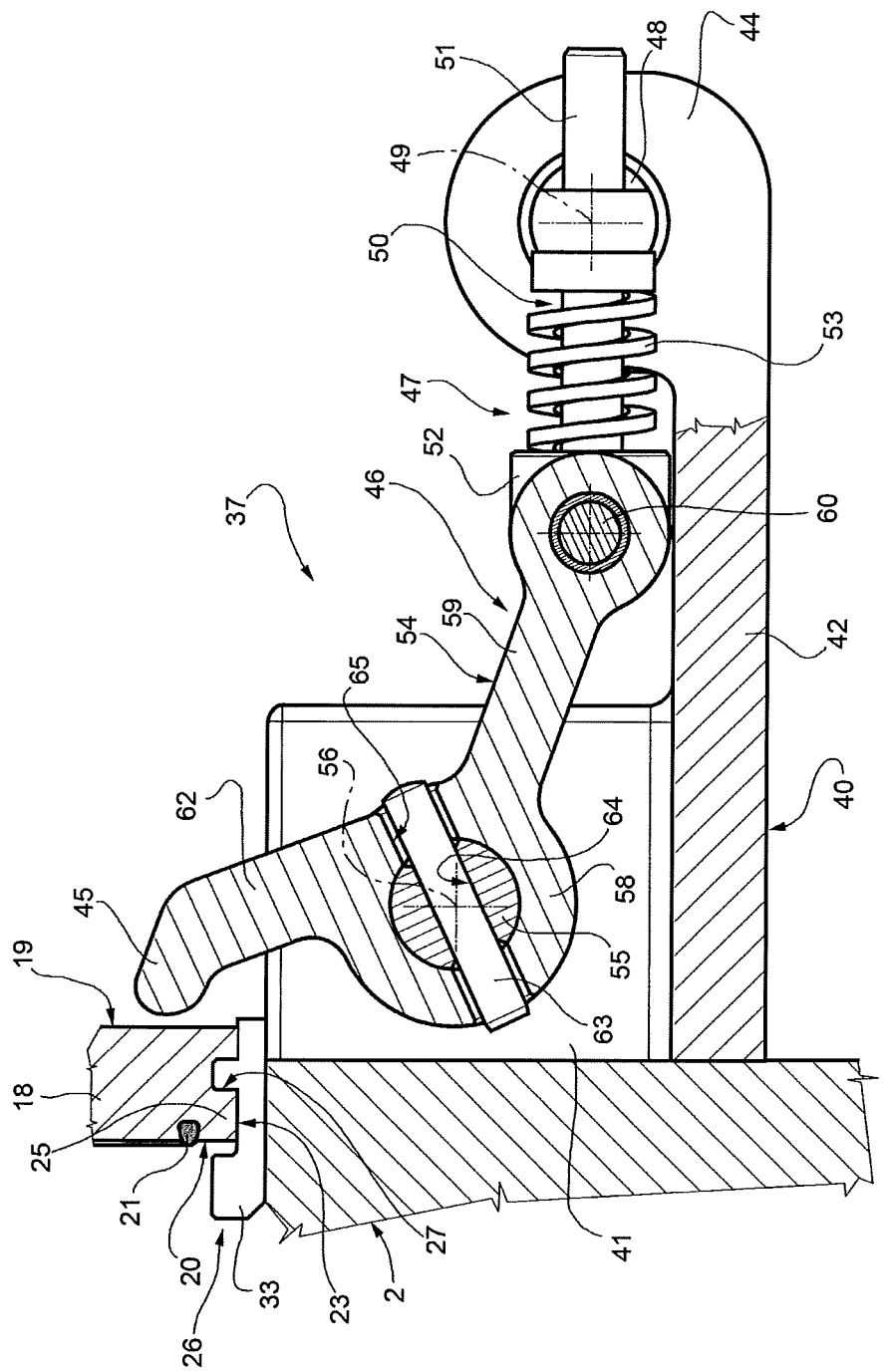
FIGS. 3 and 4 show larger-scale views of a detail in FIG. 2 in different operating configurations.
Figure 4:
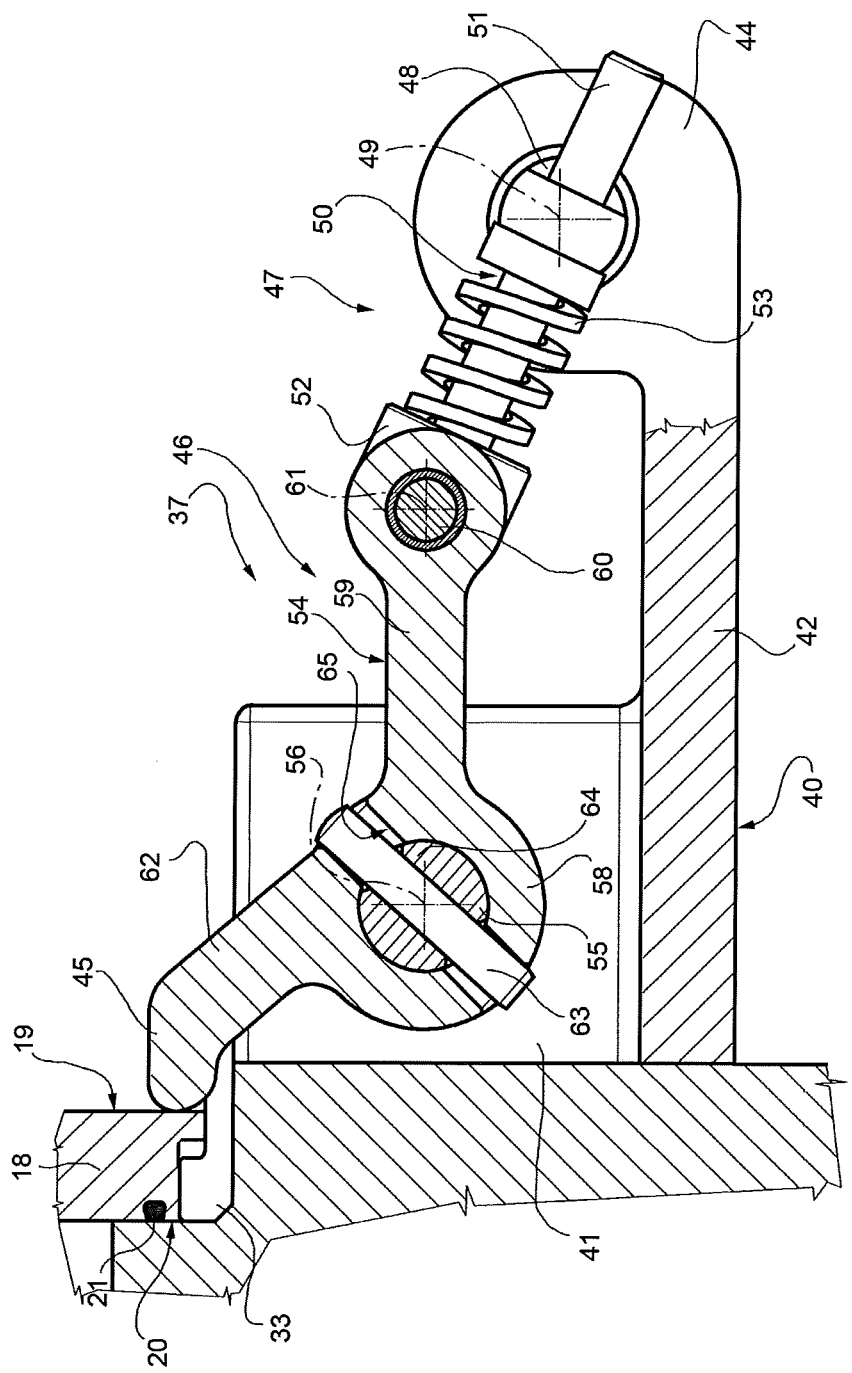

As shown in FIGS. 2, 3 and 4, each thrust mechanism 37 comprises a pressure member or finger 45; and a toggle actuating mechanism 46, which is operated by said control member to move pressure finger 45 between a withdrawn rest position (shown in FIG. 3 and on the right in FIG. 2), in which pressure finger 45 does not interfere with flange 18 and allows it to move along guides 26, and a forward work position (shown in FIG. 4 and on the left in FIG. 2), in which pressure finger 45 exerts force on flange 18 in direction 34 to seal flange 18 to rim 12.

Toggle actuating mechanism 46 includes a crank mechanism comprising a crank 47, which is operatively connected to a pin 48, fitted through a respective appendage 44 of plate 42, to oscillate along an arc of given size about a fixed axis 49 parallel to insertion direction 31, perpendicular to direction 34, and aligned with axes 49 of thrust mechanisms 37 in the same group 38.

In the example shown, crank 47 is defined by two identical levers 50 located on opposite sides of appendage 44 and each comprising a cylindrical rod 51, which is fitted in axially-sliding manner through a respective end portion of pin 48, lies in a plane perpendicular to axis 49, and has a flared head 52 on its free axial end. Each lever 50 has a coil spring 53 coiled about rod 51 and compressed between head 52 and a disk fitted in sliding manner to rod 51 and held resting against pin 48 by spring 53.

In a variation, crank 47 comprises a single lever 50.

Toggle actuating mechanism 46 also comprises a rocker arm 54, which is housed in the gap between lateral wall 4 and crank 47, and is fitted to a rocker arm shaft 55 to oscillate in a vertical plane about a fixed axis 56, which is parallel to axis 49 and located above axis 49 with respect to the plane containing plates 42 (FIGS. 3 and 4). Each rocker arm shaft 55 defines said control member for controlling thrust mechanisms 37 in a respective group 38, extends through lateral portions 43 of brackets 40 and through rocker arms 54 of group 38, and is operated manually by means of a spanner 57, or any other suitable tool, attached angularly to a connecting portion 155 (FIG. 1) formed on one or both axial ends of rocker arm shaft 55 projecting outwards of brackets 40.

As shown in more detail in FIGS. 3 and 4, rocker arm 54 is generically V-shaped, and comprises a hub 58 fitted to shaft 55; a first arm 59, which extends from hub 58 to crank 47, and is connected to the free ends of levers 50 by a hinge comprising a rocker arm pin 60 fitted in rotary manner to heads 52 of levers 50 and having a longitudinal axis 61 parallel to axes 49 and 56; and a second arm 62, which extends from hub 58 towards frame 2, forms a roughly 120° angle with arm 59, and has an end portion bent forwards towards recess 8 and defining said pressure finger 45.

By rotating shaft 55 a given amount, pressure fingers 45 of each group 38 of thrust mechanisms 37 are all operated simultaneously to move between their respective withdrawn rest positions (FIG. 3), which correspond to an idle configuration of locking device 24 and allow the operator to insert and remove emitter 3, and their respective forward work positions (FIG. 4), which correspond to a work configuration of locking device 24, and in which pressure fingers 45 engage the longitudinal edges of annular surface 20 of flange 18 to push and seal flange 18 onto rear surface 9 of respective recess 8 and so fix emitter 3 in the operating position.

In connection with the above, it is important to note that, despite being fitted to the same rocker arm shaft 55 and therefore operated simultaneously, all the rocker arms 54 in each group 38 of thrust mechanisms 37 have a certain amount of slack around axis 56, which makes them relatively independent of each other. Accordingly, and as shown in FIGS. 3 and 4, hub 58 of each rocker arm 54 has an inside diameter slightly larger than the outside diameter than shaft 55, and hub 58 and shaft 55 are connected angularly by a through pin 63, which extends crosswise through hub 58 and shaft 55, and has a centre portion pressed inside a radial hole 64 through shaft 55, and two end portions which loosely engage respective portions of a hole 65 formed through hub 58, coaxial with hole 64, and larger in diameter than pin 63. Consequently, when pressure fingers 45 are moved into the forward work position by rotation of shaft 55, and are pushed onto flange 18, each rocker arm 54 is free to rotate about axis 56 towards the withdrawn rest position by an amount proportional to the difference between the diameters of pin 63 and hole 65. This rotational slack of rocker arms 54 compensates for any unevenness of annular surface 19 of flange 18 and, at the same time, ensures the load on flange 18 is distributed substantially evenly.

When pressure finger 45 is in the withdrawn rest position, respective toggle actuating mechanism 46 assumes the configuration shown in FIG. 3, in which rocker arm 54 is rotated backwards with respect to frame 2, pressure finger 45 is located outside recess 8, first arm 59 slopes towards plate 42, and crank 47 is substantially parallel to plate 42. In this configuration, the thrust exerted by each spring 53 on pin 60 and directed along the axis of respective rod 51 generates, with respect to axis 56, an angular moment which tends to keep rocker arm 54 rotated backwards, i.e. to keep pressure finger 45 in the withdrawn rest position.

When pressure finger 45 is in the forward work position, respective toggle actuating mechanism 46 assumes the configuration shown in FIG. 4, in which rocker arm 54 is rotated forwards towards frame 2, and pressure finger 45 extends inside recess 8 to exert pressure in direction 34 on annular surface 19 of flange 18 and, together with the other pressure fingers 45, to seal annular surface 20 of flange 18 to rim 12 of rear surface 9 of recess 8. In this configuration, arm 59 is substantially parallel to plate 42, and crank 47 slopes at such an angle to plate 42 that the thrust exerted by each spring 53 generates, with respect to axis 56, an angular moment which tends to rotate rocker arm 54 forwards, i.e. to push pressure finger 45 against flange 18.

Operation of sterilization unit 1 will now be described as of the configuration shown on the right in FIG. 2, in which emitter 3 is in the idle position, in which flange 18 is inserted inside recess 8, is positioned facing opening 11, is detached from rear surface 9 of recess 8, and is supported by frame 2, by its axial end portions resting on blocks 32 and stops 35.

When emitter 3 is in the idle position, locking device 24 is in the idle configuration, and pressure fingers 45 are in their respective withdrawn rest positions.

When locking device 24 is activated by the operator rotating rocker arm shafts 55, rocker arms 54 rotate about respective axes 56 to move pressure fingers 45 towards flange 18.

In connection with the above, it should be pointed out that shafts 55 may be completely independent of one another, as in the example shown, so the two groups 38 on the same side of frame 2 can be activated separately and successively; or, in a variation not shown, the two shafts 55 may be connected angularly by a transmission mechanism, so that rotation of one shaft 55 is transmitted to the other to move thrust mechanisms 37 of both groups 38 simultaneously.

It should also be pointed out that, though the sterilization unit 1 shown and described herein comprises two emitters 3 on opposite sides of channel 6, the locking system based on the use of thrust mechanisms 37 is specular with respect to the plane of symmetry P of channel 6 and may therefore theoretically also be used, with no alterations, on a sterilization unit with only one emitter 3 on one side of channel 6.

Referring again to FIG. 2, they move, pressure fingers 45 intercept and push flange 18 in direction 34, so that flange 18, guided by blocks 32 and stops engaging portions 28, moves parallel to itself towards the rear of recess 8.

The instant annular surface 20 of flange 18 contacts rim 12, each toggle actuating mechanism 46 is close to reaching its dead centre position, i.e. the position in which the 'toggle' defined by arm 59 and crank 47 is extended, and pressure finger 45 exerts maximum thrust.

From this point on, as shaft 55 is rotated further, toggle actuating mechanism 46 first moves into the dead centre position, thus pressing seal 21 to seal flange 18 to rim 12, and then past the dead centre position into the final lock position shown in FIG. 4. This is an irreversible lock position, from which toggle actuating mechanism 46 can never back off independently, even if subjected to relatively severe accidental external stress or forces induced by deformation of flange 18 as a result of in-service thermal expansion or machine vibrations.

The toggle system described above also has the advantage of toggle actuating mechanism 46 clicking into the final lock position, which is thus clearly perceptible by the operator rotating shaft 55, and prevents the operator from rotating shaft 55 past the final lock position, which would not only be pointless, but could also potentially ruin or at least damage locking device 24.

Finally, another important advantage to note is the way in which locking device 24 is designed to exert controlled force on flange 18, i.e. a force that ensures flange 18 seals to frame 2, but at the same time allows flange 18 to deform as a result of thermal expansion, but without the stress produced by this deformation buckling or bending foil 16. This is achieved by virtue of the thrust exerted by springs 53 determining the lock pressure exerted by pressure fingers 45 on flange 18. By adjusting the preload on springs 53, it is therefore possible to set a target lock force and so avoid overstressing flange 18.

The invention claimed is:

1. An electron beam sterilization unit for processing food packaging material, the unit comprising:
   a frame;
   at least one electron beam emitter fitted to the frame, along a path of material for processing, the at least one electron beam emitter having a flange for connection to the frame; and
   a locking device fitted to the frame to lock the emitter with respect to the frame in a work position, the locking device comprising a thrust system configured to exert a lock force on said flange in a first direction perpendicular to a second direction along which the flange is inserted into the frame, and an actuation system configured to activate the thrust system, the actuation system comprising a rotatable toggle actuating system rotating at least a portion of the thrust system forward with respect to the frame to lock the flange of the emitter to the frame.

2. The unit as claimed in claim 1, wherein the frame comprises
   at least one fixed guide extending in the second direction perpendicular to said first direction, and
   a channel along which the material for processing travels, and which communicates with the outside through at least one opening bounded outwards by a flat rim crosswise to said first direction,
   wherein the flange comprises a connecting system configured to engage said guide in sliding manner, and configured to allow the emitter to translate in the second direction to and from an idle position, in which the flange is positioned facing said opening and at a given distance from said rim.

3. The unit as claimed in claim 2, wherein the flange comprises a center portion and two end portions, said connecting system being configured so that, when the emitter is in the idle and work positions, the flange rests on the guide solely by said end portions.

4. The unit as claimed in claim 2, wherein, when the emitter is in the idle position, the connecting system engages the guide in a transversely sliding manner, to allow the flange to translate, parallel to itself, in the first direction, and to move the emitter from the idle position to the work position, in which the flange is sealed to said rim.

5. The unit as claimed in claim 1, wherein the thrust system comprises a plurality of pressure members, and
   the toggle actuating system comprises a plurality of toggle mechanisms, each of the toggle mechanisms being associated with a respective pressure member and movable between a rest position, in which the pressure member does not engage the flange, and a work position, in which the pressure member exerts a force in the first direction on the flange.

6. The unit as claimed in claim 5, wherein the toggle mechanisms divided into two groups located on opposite sides of the flange to cooperate, in use, with respective peripheral portions of the flange, the actuating system comprising, for each group of toggle mechanisms, a control member configured to activate the respective toggle mechanism.

7. The unit as claimed in claim 6, wherein each toggle mechanism comprises
   a crank that rotates about a fixed first axis crosswise to the first direction, and
   a rocker arm interposed between the crank and the frame, the rocker arm comprising a first arm and a second arm arranged in a V-shape, and being hinged about a second axis, parallel to the first axis, to oscillate in a plane parallel to the first direction, the first arm being connected by a hinge pin to a free end of the crank to define a toggle with the crank, and to oscillate about a third axis parallel to the first axis, the second arm having a free end portion, which extends towards the frame and defines said pressure member for the respective toggle mechanism.

8. The unit as claimed in claim 7, wherein each control member is defined by a respective shaft coaxial with the second axis, the rocker arm comprising a center hub connected angularly to said shaft with an amount of rotational slack.

9. The unit as claimed in claim 7, wherein the rest position and work position of the respective toggle mechanism are located on either side of a dead center position, in which said toggle is extended and the pressure member exerts maximum thrust.

10. The unit as claimed in claim 7, wherein the pressure member and the first axis are located on opposite sides of the second axis, the crank being hinged on a pin rotatable about the first axis and comprising at least one lever, which has a first end portion engaging in an axially sliding manner a radial hole through said pin, and a second end portion connected to the first arm by said hinge pin,
wherein an elastic system is interposed between said first end portion and the second end portion to exert on said hinge pin a preselected amount of thrust directed perpendicularly to the third axis.

11. An electron beam sterilization unit for processing food packaging material, the unit comprising:
a frame;
at least one electron beam emitter fitted to the frame along a path of the food packaging material, the at least one electron beam emitter comprising:
a casing housing a gun that accelerates electrons;
a flange connectable to the frame; and
a foil extending across a window in the flange; and
a locking device fitted to the frame to lock the emitter relative to the frame in a work position, the locking device comprising an arm mounted on a rotatable shaft to rotate together with the shaft, the arm possessing an end adjacent the flange, the arm including a pressure finger at the end of the arm adjacent the flange to contact the flange as the shaft and flange are rotated and to urge the flange of the emitter into sealing contact with the frame.

12. The unit as claimed in claim 11, wherein the locking device comprises a plurality of arms mounted on the shaft to rotate together with the shaft, each arm possessing an end adjacent the flange, each arm including a pressure finger at the end of the arm adjacent the flange to contact the flange and urge the flange of the emitter into sealing contact with the frame.

13. The unit as claimed in claim 11, wherein the flange includes two sides and comprises a pair of runners, each runner being positioned along one of the sides of the flange, each flange being fitted in and movable along a respective guide on the frame.

14. The unit as claimed in claim 11, wherein the locking device includes a crank mounted to oscillate about an axis, the arm being a first arm of a rocker arm that also includes a second arm, the crank including an end portion that directly contacts the second arm.

15. The unit as claimed in claim 14, wherein the locking device comprises a plurality of arms mounted on the shaft to rotate together with the shaft, the plurality of arms constituting a first group of arms located along one side of the flange, the locking device further comprising a second group of arms located on an opposite side of the flange and each including a pressure finger to contact the flange and urge the flange of the emitter into sealing contact with the frame.

16. The unit as claimed in claim 11, wherein the locking device includes
a rod mounted to oscillate about an axis and a head at one end of the rod, the rod being slidingly fitted in a pin so that the rod is slidable relative to the pin, and
a spring surrounding the rod and positioned between the head and the pin,
wherein the arm is a first arm of a rocker arm that also includes a second arm, the head directly contacting the second arm.

17. The unit as claimed in claim 11, wherein the arm rotates about an axis of the rotatable shaft to rotate together with the shaft.

18. An electron beam sterilization unit for processing food packaging material, the unit comprising:
a frame;
at least one electron beam emitter fitted to the frame, along a path of material for processing, the at least one electron beam emitter having a flange for connection to the frame; and
a locking device fitted to the frame to lock the emitter with respect to the frame in a given work position, the locking device comprising a thrust system configured to exert a lock force on said flange in a first direction, and an actuation system configured to activate the thrust system, the actuation system comprising a toggle actuating system including at least one toggle mechanism comprising
a crank that rotates about a fixed first axis crosswise to the first direction, and
a rocker arm interposed between the crank and the frame, the rocker arm comprising a first arm and a second arm arranged in a V-shape and being hinged about a second axis, parallel to the first axis, to oscillate in a plane parallel to the first direction, the first arm being connected by a hinge pin to a free end of the crank to define a toggle with the crank, and to oscillate about a third axis parallel to the first axis, the second arm having a free end portion, which extends towards the frame and locks the flange to the frame.

* * * * *